(12) United States Patent
Rittermeier et al.

(10) Patent No.: US 11,267,703 B2
(45) Date of Patent: Mar. 8, 2022

(54) METHOD AND A SYSTEM FOR SEPARATING AND TREATING IMPURITIES FROM A HYDROGEN CHLORIDE LIQUID MIXTURE

(71) Applicant: Covestro Deutschland AG, Leverkusen (DE)

(72) Inventors: Andre Rittermeier, Leverkusen (DE); Rainer Hellmich, Cologne (DE); Alfred Soppe, Issum (DE); Luyan Wu, Shanghai (CN); Micky Qian, Shanghai (CN); Peter Lehner, Mühlheim an der Ruhr (DE); Jürgen Bittner; Friedhelm Steffens, Leverkusen (DE); Henrike Fink, Meerbusch (DE); Eric Jakobs, Krefeld (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/312,358

(22) PCT Filed: Jun. 30, 2017

(86) PCT No.: PCT/EP2017/066354
§ 371 (c)(1),
(2) Date: Dec. 21, 2018

(87) PCT Pub. No.: WO2018/002342
PCT Pub. Date: Jan. 4, 2018

(65) Prior Publication Data
US 2019/0194018 A1  Jun. 27, 2019

(30) Foreign Application Priority Data

Jun. 30, 2016 (CN) .......................... 201610527670.8

(51) Int. Cl.
*C01B 7/07* (2006.01)
*C07C 263/10* (2006.01)
*C07C 263/20* (2006.01)

(52) U.S. Cl.
CPC .......... *C01B 7/0712* (2013.01); *C07C 263/10* (2013.01); *C07C 263/20* (2013.01)

(58) Field of Classification Search
CPC .... C01B 7/0712; C07C 263/20; C07C 263/10
See application file for complete search history.

(56) References Cited

U.S. PATENT DOCUMENTS 3,597,156 A * 8/1971 Solomon ............... C01B 7/0706
423/488
7,584,629 B2  9/2009 Sohn et al.
(Continued)

FOREIGN PATENT DOCUMENTS

CN  102989291 A  3/2013
DE  10260084 A1  7/2004
(Continued)

OTHER PUBLICATIONS

Gaspard et al, Biomass for Sustainable Applications Pollution Remediation and Energy, Chapter 5, 2014, p. 242. (Year: 2014).*
(Continued)

*Primary Examiner* — Amy C Bonaparte
(74) *Attorney, Agent, or Firm* — Faegre Drinker Biddle & Reath LLP

(57) ABSTRACT

The present invention relates to a method and a system for separating and treating impurities from a hydrogen chloride liquid mixture from the process for preparing isocyanate with phosgenation including sending hydrogen chloride liquid mixture into a gas-liquid separation column for separation to yield a liquid phase flow with impurities at the bottom of the gas-liquid separation column, neutralizing the
(Continued)

liquid phase flow comprising impurities with an alkaline liquid in the neutralization tank to yield a neutralized solution, and sending the neutralized solution into a waste liquid treatment device from said neutralization tank for treatment.

16 Claims, 5 Drawing Sheets

(56) References Cited

U.S. PATENT DOCUMENTS

| 8,692,016 | B2 | 4/2014 | Sanders et al. | |
|---|---|---|---|---|
| 2006/0123842 | A1* | 6/2006 | Sohn | C01B 7/0731 |
| | | | | 62/617 |
| 2007/0043233 | A1* | 2/2007 | Sanders | C07C 263/10 |
| | | | | 560/347 |

FOREIGN PATENT DOCUMENTS

| EP | 1080767 A2 * | 3/2001 | ............... C01C 1/18 |
|---|---|---|---|
| EP | 1754698 A2 | 2/2007 | |
| GB | 669671 A | 4/1952 | |
| GB | 1355247 A | 6/1974 | |
| JP | 2008-529939 A | 8/2008 | |
| WO | 2006/084832 A1 | 8/2006 | |

OTHER PUBLICATIONS

International Search Report for PCT/EP2017/066354 dated Oct. 4, 2017.
Written Opinion of the International Searching Authority for PCT/EP2017/066354 dated Oct. 4, 2017.
International Preliminary Report on Patentability received for PCT Patent Application No. PCT/EP2017/066354, dated Jan. 10, 2019, 9 pages.

* cited by examiner

US 11,267,703 B2

METHOD AND A SYSTEM FOR SEPARATING AND TREATING IMPURITIES FROM A HYDROGEN CHLORIDE LIQUID MIXTURE

CROSS-REFERENCE TO RELATED APPLICATIONS

This application is a national stage application (under 35 U.S.C. § 371) of PCT/EP2017/066354, filed Jun. 30, 2017, which claims benefit of Chinese Application No. 201610527670.8, filed Jun. 30, 2016, both of which are incorporated herein by reference in their entirety.

TECHNICAL FIELD

The present invention relates to a method and a system for separating and treating impurities from a hydrogen chloride liquid mixture, and particularly relates to a method and a system of separating and treating impurities from a hydrogen chloride liquid mixture produced from the process for preparing isocyanate with phosgenation.

BACKGROUND OF THE INVENTION

The process for preparing isocyanate with phosgenation produces gas mixtures comprising hydrogen chloride. These gas mixtures containing hydrogen chloride normally requires further partial liquefaction, for example, a rectification column partial liquefaction treatment to yield a hydrogen chloride gas and a hydrogen chloride liquid mixture. The hydrogen chloride gas returns to the phosgenation reaction unit for recycling and the hydrogen chloride liquid mixture is treated and sent to incineration.

The process for treating hydrogen chloride liquid mixture generally comprises: sending the hydrogen chloride liquid mixture comprising impurities into a gas-liquid separation column, evaporating and separating to yield a gas phase flow comprising hydrogen chloride gas and a liquid phase flow comprising impurities and sending the liquid phase flow comprising impurities into the incinerator for incineration. In this method of separating and treating impurities, blocking often occurs at the outlet of the gas-liquid separation column, the liquid phase flow pipeline and the valve, resulting in frequent shutdowns of the hydrogen chloride liquid mixture separation and treatment unit for maintenance, and thereby renders frequent shutdowns of the system for preparing isocyanate with phosgenation.

There is an urgent need in the industry to find the reasons causing the blocking of the liquid flow pipeline, the valve and the gas-liquid separation column in the process of separating and treating impurities from a hydrogen chloride liquid mixture, and provide a solution to obtain a method that does not require frequent shutdowns.

SUMMARY OF THE INVENTION

One of the objects of the present invention is to provide a method of separating and treating impurities from a hydrogen chloride liquid mixture.

Another object of the present invention is to provide a system for separating and treating impurities from a hydrogen chloride liquid mixture.

A further object of the present invention is to provide a process for preparing isocyanate with phosgenation.

Another object of the present invention is to provide a system for preparing isocyanate with phosgenation.

The present invention discovers that the hydrogen chloride liquid mixture produced by the process for preparing isocyanate with phosgenation comprises ammonium chloride impurities. The ammonium chloride impurities constantly deposit at the outlet of the gas-liquid separation column, the liquid phase flow pipeline and the valve, causing blocking. Shutdown of the hydrogen chloride liquid mixture separation and treatment unit for maintenance is thus frequently required, resulting in frequent shutdowns of the system for preparing isocyanate with phosgenation.

The present invention provides a method and a system for separating and treating impurities from a hydrogen chloride liquid mixture which does not require frequent shutdowns for maintenance, solving the problem of the blocking of the liquid phase flow pipeline, the valve and the gas-liquid separation column due to impurity deposition, and reducing the shutdown frequency for maintenance of the hydrogen chloride liquid mixture separation and treatment unit.

The term "flow into" should generally be understood as that the liquid phase flow comprising impurities is discharged from a higher position to a lower position in the case where no external force, except for gravity, is applied and the liquid phase flow pipeline is not bent. The liquid phase flow pipeline is preferably as perpendicular as possible to reduce the deposition of the liquid phase flow comprising impurities in the liquid phase flow pipeline, the valve and the gas-liquid separation column.

The term "below" should generally be understood as right below or slanting below.

The present invention discloses a method of separating and treating impurities from a hydrogen chloride liquid mixture, comprising the steps of:

sending said hydrogen chloride liquid mixture into a gas-liquid separation column for separation to yield a liquid phase flow comprising impurities at the bottom of said gas-liquid separation column, and said impurities comprising ammonium chloride;

making said liquid phase flow comprising impurities flow into a neutralization tank through a liquid phase flow pipeline L1 from the bottom of said gas-liquid separation column, neutralizing said liquid phase flow comprising impurities with an alkaline liquid in said neutralization tank to yield a neutralized solution; and sending the neutralized solution into a waste liquid treatment device from said neutralization tank for treatment.

Said neutralization tank is arranged below said gas-liquid separation column, and the pressure in said neutralization tank is preferably not higher than the pressure in said gas-liquid separation column, and more preferably lower than the pressure in said gas-liquid separation column. The pressure in said neutralization tank is preferably atmospheric pressure.

A buffer tank may be further arranged between said gas-liquid separation column and said neutralization tank. One end of said buffer tank is connected to the bottom of the gas-liquid separation column, and the other end of the buffer tank is connected to the neutralization tank, such that the liquid phase flow comprising impurities sequentially flows into said buffer tank from the bottom of said gas-liquid separation column through said liquid phase flow pipeline L1, and then flows into the neutralization tank through a liquid phase flow pipeline L2 from said buffer tank.

When a buffer tank is further arranged between said gas-liquid separation column and the neutralization tank, said buffer tank is preferably arranged below the gas-liquid separation column. The pressure in said buffer tank is preferably not higher than the pressure in the gas-liquid separation column, and the pressure in said neutralization tank is preferably not higher than the pressure in said buffer tank; the pressure in said neutralization tank is further preferably lower than the pressure in said gas-liquid separation column, and is more preferably atmospheric pressure.

The volume of said liquid phase flow comprising impurities buffered in said buffer tank preferably does not exceed 90% of the volume of said buffer tank.

The liquid phase flow pipeline is further purged with an inert gas after said liquid phase flow comprising impurities flows through said liquid phase flow pipeline L1 and/or liquid phase flow pipeline L2.

Said inert gas is preferably nitrogen.

The pH value of said neutralized solution is preferably not less than 8, more preferably not less than 10.

Said alkaline liquid is selected from one or more of the following group consisting of: alkali metal hydroxides, alkaline earth metal hydroxides, preferably one or more of the following group consisting of: sodium hydroxide, potassium hydroxide.

Said alkaline liquid may be placed in the neutralization tank in advance before said liquid phase flow comprising impurities flows into the neutralization tank, or may also be added into the neutralization tank during or after said liquid phase flow comprising impurities flows into the neutralization tank. Said alkaline liquid is preferably placed in the neutralization tank in advance before said liquid phase flow comprising impurities flows into the neutralization tank, and the volume of the alkaline liquid placed in said neutralization tank is preferably not more than 10% of the volume of said neutralization tank.

The concentration of said alkaline liquid is preferably such that the neutralized solution obtained by the neutralization reaction does not have any crystal precipitation.

The hydrogen chloride liquid mixture may comprise hydrogen chloride, ammonium chloride, phosgene and chlorobenzene compounds. Preferably, said hydrogen chloride liquid mixture is obtained by treating the gas mixture comprising hydrogen chloride obtained from the process for preparing isocyanate with phosgenation.

A gas phase flow comprising hydrogen chloride gas may be obtained at the top of said gas-liquid separation column. Said gas phase flow comprising hydrogen chloride gas comprises hydrogen chloride gas and phosgene. The hydrogen chloride gas is absorbed with water or an alkaline liquid, and the phosgene is decomposed and removed.

Said waste liquid treatment device may be a waste liquid incinerator.

Said method is a continuous or batch operation.

The starting temperature of said neutralization reaction is from 0 to 80° C., preferably at room temperature, and further preferably the temperature at which the reaction heat released by the neutralization reaction can be absorbed by the neutralized solution as much as possible.

Said method may further comprise the step of obtaining said hydrogen chloride liquid mixture from a process for preparing isocyanate with phosgenation.

The present invention also discloses a system for separating and treating impurities from a hydrogen chloride liquid mixture, comprising:

a gas-liquid separation column for receiving and separating said hydrogen chloride liquid mixture to yield a liquid phase flow comprising impurities, and said impurities comprising ammonium chloride;

a neutralizing tank for receiving said liquid phase flow comprising impurities, said liquid phase flow comprising impurities flowing into said neutralizing tank from the bottom of said gas-liquid separation column through a liquid phase flow pipeline L1, neutralizing said liquid phase flow comprising impurities with an alkaline liquid in said neutralization tank to yield a neutralized solution; and;

a waste liquid treatment device for receiving and treating said neutralized solution from said neutralization tank.

Said neutralization tank is arranged below said gas-liquid separation column. The pressure in said neutralization tank is preferably not higher than the pressure in the gas-liquid separation column, more preferably lower than the pressure in the gas-liquid separation column, and most preferably atmospheric pressure.

An inert gas purge device and an exhaust discharge device may also be arranged on said liquid phase flow pipeline L1 for purging said liquid phase flow pipeline L1 with the inert gas after said liquid phase flow comprising impurities flows through said liquid phase flow pipeline L1.

A buffer tank can be further arranged between said gas-liquid separation column and said neutralization tank for buffering said liquid phase flow comprising impurities, said liquid phase flow comprising impurities flowing into said neutralizing tank from said gas-liquid separation column, and said liquid phase flow comprising impurities sequentially flows into said buffer tank from the bottom of said gas-liquid separation column through said liquid phase flow pipeline L1, and then flows into the neutralization tank through a liquid phase flow pipeline L2 from the buffer tank.

When said system further comprises a buffer tank, said buffer tank is arranged below said gas-liquid separation column, and said neutralization tank is arranged below said buffer tank. The pressure in said buffer tank is preferably not higher than the pressure in said gas-liquid separation column, and the pressure in said neutralization tank is preferably not higher than the pressure in said buffer tank; the pressure in said neutralization tank is further preferably lower than the pressure in said gas-liquid separation column, and is more preferably atmospheric pressure.

An inert gas purge device and an exhaust discharge device may also be arranged on said liquid phase flow pipeline L2 for purging said liquid phase flow pipeline L2 with the inert gas after said liquid phase flow comprising impurities flows through said liquid phase flow pipeline L2.

Said inert gas is preferably nitrogen.

Said buffer tank is provided with a liquid level control device to ensure that the volume of the liquid phase flow comprising impurities buffered in said buffer tank does not exceed 90% of said buffer tank volume. Said liquid level control device may be a liquid level control device commonly used in the industry.

Said alkaline liquid may be placed in the neutralization tank in advance before said liquid phase flow comprising impurities flows into the neutralization tank, or may be added to the neutralization tank during or after said liquid phase flow comprising impurities flows into the neutralization tank. Said alkaline liquid is preferably placed in the neutralization tank in advance before said liquid phase flow comprising impurities flows into the neutralization tank, and the alkaline liquid placed in said neutralization tank preferably has a volume not exceeding 10% of the volume of said neutralization tank.

Said neutralization tank may be equipped with a liquid circulation pump to keep the alkaline liquid circulating inside the neutralization tank.

Said neutralization tank may be equipped with a cooler to remove the heat produced by the neutralization reaction.

A gas phase flow comprising hydrogen chloride gas can be obtained at the top of said gas-liquid separation column.

The system of the present invention further comprises a hydrogen chloride absorption column, a phosgene decomposer and a central thermal oxidizer. The hydrogen chloride absorption column is used for absorbing the hydrogen chloride gas in the gas phase flow comprising hydrogen chloride gas obtained from the top of the gas-liquid separation column. The phosgene decomposer and the central thermal oxidizer are used for decomposing the phosgene in the gas phase flow comprising hydrogen chloride gas.

The waste liquid treatment device may be a waste liquid incinerator.

The present invention further discloses a method of preparing isocyanate with phosgenation, comprising the steps of:

obtaining an isocyanate product and a gas mixture comprising hydrogen chloride from the phosgenation reaction process;

treating said gas mixture comprising hydrogen chloride to yield a hydrogen chloride liquid mixture; and separating and treating said hydrogen chloride liquid mixture according to a method of separating and treating impurities from a hydrogen chloride liquid mixture as disclosed in the present invention.

The method of treating the gas mixture comprising hydrogen chloride to yield a hydrogen chloride liquid mixture can be partial liquefaction or other well-known methods in the industry.

The pressure in said gas-liquid separation column is preferably 5 to 25 bar gauge pressure, most preferably 7 to 15 bar gauge pressure; the temperature is preferably 0 to 150° C., more preferably 15 to 100° C., most preferably 15 to 80° C.

The pressure in said buffer tank is preferably 0 to 10 bar gauge pressure, most preferably 0 to 5 bar gauge pressure.

The present invention further discloses a system for preparing isocyanate with phosgenation, comprising:

a phosgenation reaction unit for carrying out a phosgenation reaction to yield an isocyanate product and a gas mixture comprising hydrogen chloride;

a hydrogen chloride-containing gas mixture treatment unit for treating said gas mixture containing hydrogen chloride to yield a hydrogen chloride liquid mixture; and a hydrogen chloride liquid mixture separation and treatment unit for separating and treating said hydrogen chloride liquid mixture according to a system for separating and treating impurities from a hydrogen chloride liquid mixture as disclosed in the present invention.

The treatment method of said hydrogen chloride-containing gas mixture treatment unit can be partially liquefying or other well-known methods in the industry.

The present invention has the following advantages: by allowing the liquid phase flow comprising impurities to have a neutralization reaction with the alkaline liquid, it prevents the impurities, in particular ammonium chloride therein, from depositing and blocking in the liquid phase flow pipeline, the valve and the gas-liquid separation column. The present invention also realizes a smooth flowing of the liquid phase flow and reduces deposition by arranging the relative positions between the devices. Further, the present invention arranges the inert gas purge device on the liquid phase flow pipelines among the gas-liquid separation column, the buffer tank and the neutralization tank to purge and remove the liquid phase flow comprising impurities from the liquid phase flow pipeline, thus preventing the impurities from depositing and blocking in the liquid phase flow pipeline and the valve, and reducing the shutdown frequency for maintenance of the system for preparing isocyanate with phosgenation.

DESCRIPTION OF THE DRAWINGS

The drawings and the Examples of the present invention are exemplary rather than limiting.

The following further describes the present invention in detail with drawings and embodiments.

DETAILED DESCRIPTION

The present invention discloses a method and a system for separating and treating impurities from a hydrogen chloride liquid mixture.

For the method of separating and treating impurities from a hydrogen chloride liquid mixture as described in the present invention, the hydrogen chloride liquid mixture comprising impurities may come from the system for preparing isocyanate with phosgenation, and may also come from other systems that can produce hydrogen chloride liquid mixture comprising ammonium chloride impurities.

Figure 1:
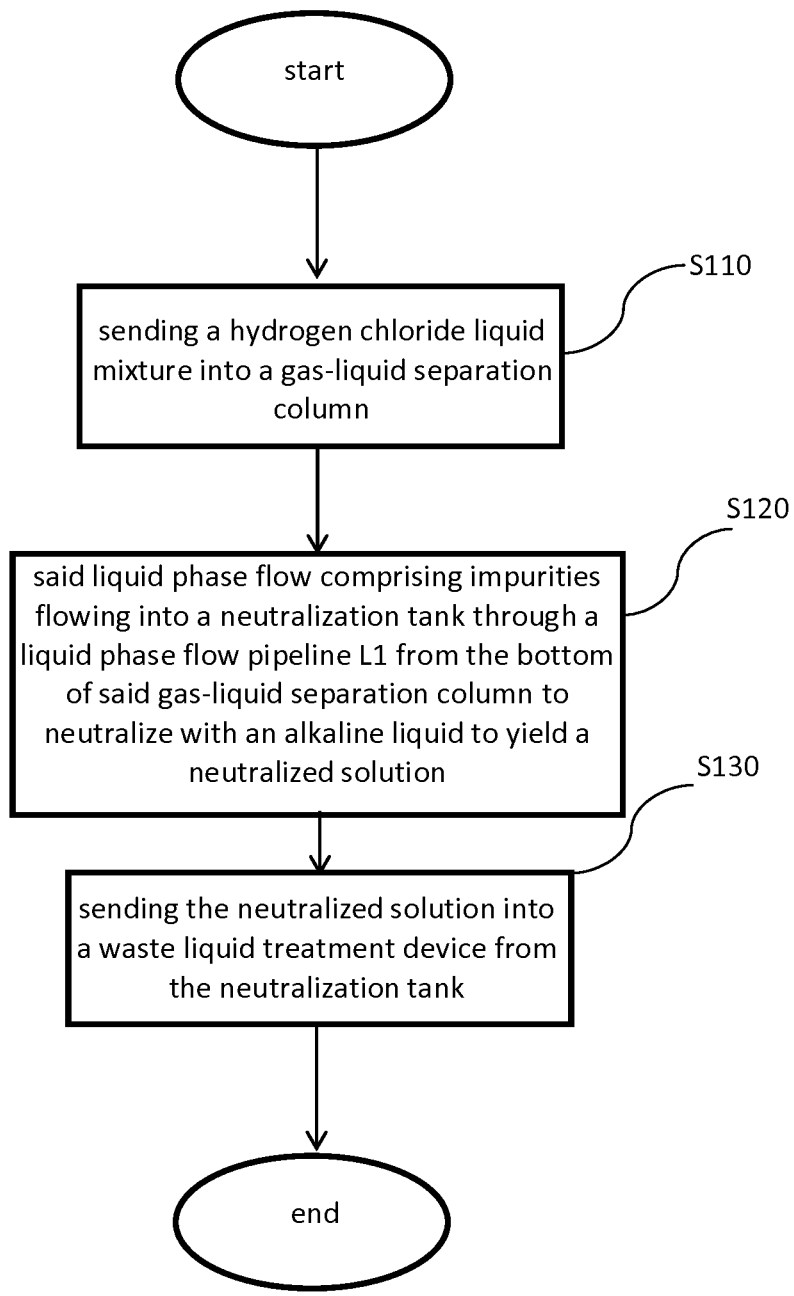
FIG. 1 is an exemplary flow chart for the method of separating and treating impurities from a hydrogen chloride liquid mixture in accordance with one Example of the present invention.

FIG. 1 is an exemplary flow chart for the method of separating and treating impurities from a hydrogen chloride liquid mixture in accordance with one Example of the present invention. In step S110, the hydrogen chloride liquid mixture enters a gas-liquid separation column for separation to yield a liquid phase flow comprising impurities. In step S120, the liquid phase flow comprising impurities flows into a neutralization tank through a liquid phase flow pipeline L1 from the bottom of the gas-liquid separation column, which has a neutralization reaction with the alkaline liquid in the neutralization tank to yield a neutralized solution. In step S130, the neutralized solution enters a waste liquid treatment device from the neutralization tank for treatment.

Figure 2:
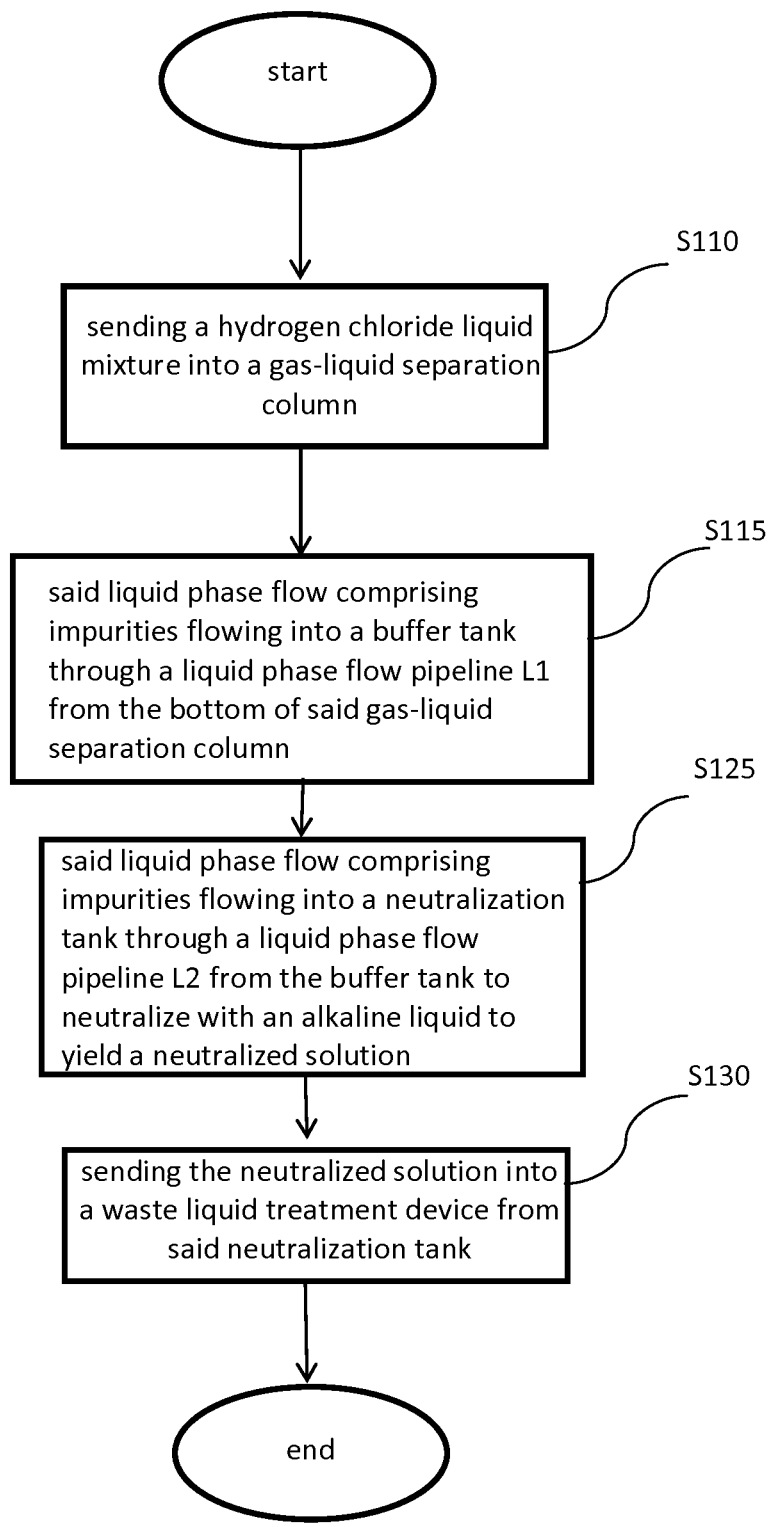
FIG. 2 is an exemplary flow chart for the method of separating and treating impurities from a hydrogen chloride liquid mixture in accordance with one Example of the present invention.

FIG. 2 is an exemplary flow chart for the method of separating and treating impurities from a hydrogen chloride liquid mixture in accordance with one Example of the present invention. In step S110, the hydrogen chloride liquid mixture enters a gas-liquid separation column for separation to yield a liquid phase flow comprising impurities. In step S115, the liquid phase flow comprising impurities flows into a buffer tank through a liquid phase flow pipeline L1 from the bottom of the gas-liquid separation column. In step S125, the liquid phase flow comprising impurities flows into a neutralization tank through a liquid phase flow pipeline L2 from the buffer tank, which has a neutralization reaction with the alkaline liquid placed in the neutralization tank to yield a neutralized solution. In step S130, the neutralized solution enters a waste liquid treatment device from the neutralization tank for treatment.

Figure 3:
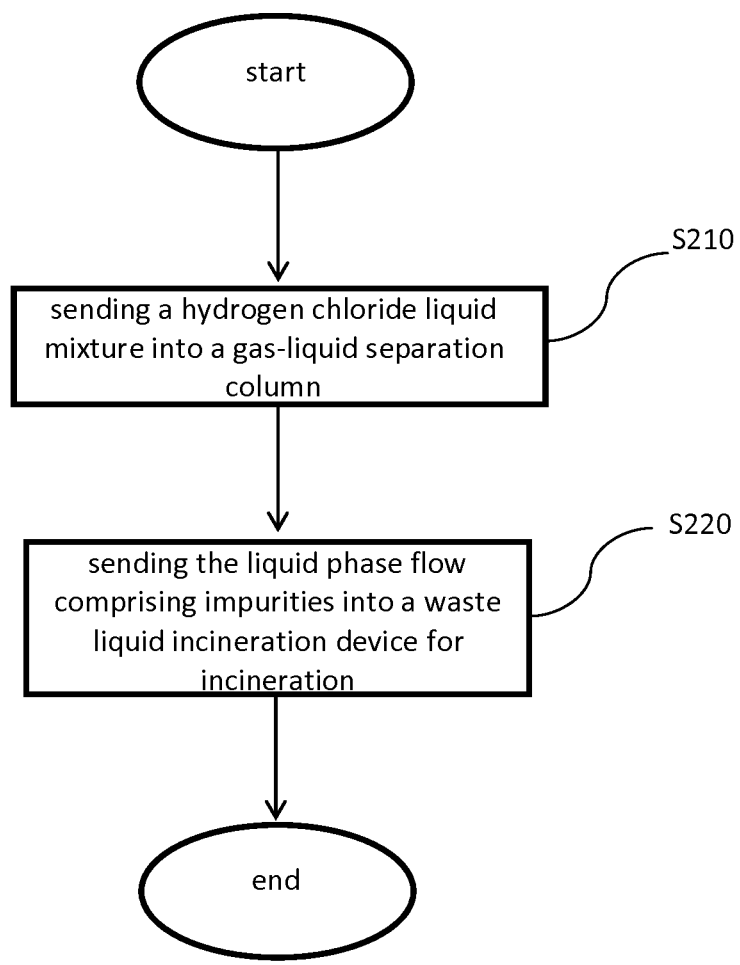
FIG. 3 is an exemplary flow chart for the method of separating and treating impurities from a hydrogen chloride liquid mixture in accordance with one Comparative Example of the present invention.

FIG. 3 is an exemplary flow chart for the method of separating and treating impurities from a hydrogen chloride liquid mixture in accordance with one Comparative Example of the present invention. In step S210, the hydrogen chloride liquid mixture enters a gas-liquid separation column for separation to yield a liquid phase flow comprising impurities. In step S220, the liquid phase flow comprising impurities enters a waste liquid incineration device for incineration.

Figure 4:
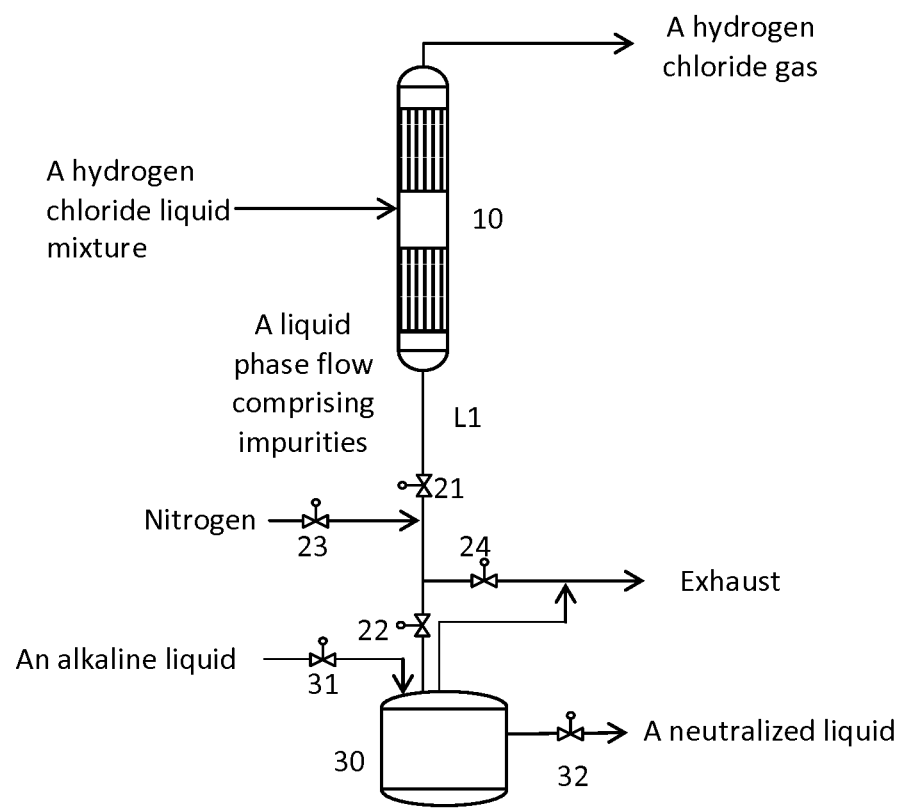
FIG. 4 is an exemplary figure of the system for separating and treating impurities from a hydrogen chloride liquid mixture in accordance with one Example of the present invention.

FIG. 4 is an exemplary figure of the system for separating and treating impurities from a hydrogen chloride liquid in accordance with one Example of the present invention. A gas-liquid separation column 10 is connected with a neutralization tank 30 through a liquid phase flow pipeline L1 which is equipped with an upper discharge valve 21 and a lower discharge valve 22, which allow the liquid phase flow to flow into the neutralization tank 30 from the gas-liquid separation column 10. The liquid phase flow pipeline L1 is further equipped with a nitrogen purge valve 23 and an exhaust discharge valve 24, which are used to purge and remove the liquid phase flow comprising impurities remained in the liquid phase flow pipeline L1 after the liquid phase flow comprising impurities flows through the liquid phase flow pipeline L1. The neutralization tank 30 is equipped with an alkaline liquid feed valve for adding alkaline liquid. The neutralization tank 30 is further equipped with a liquid discharge valve 32 for allowing the neutralized solution in the neutralization tank 30 to enter the waste liquid treatment device for treatment.

Figure 5:
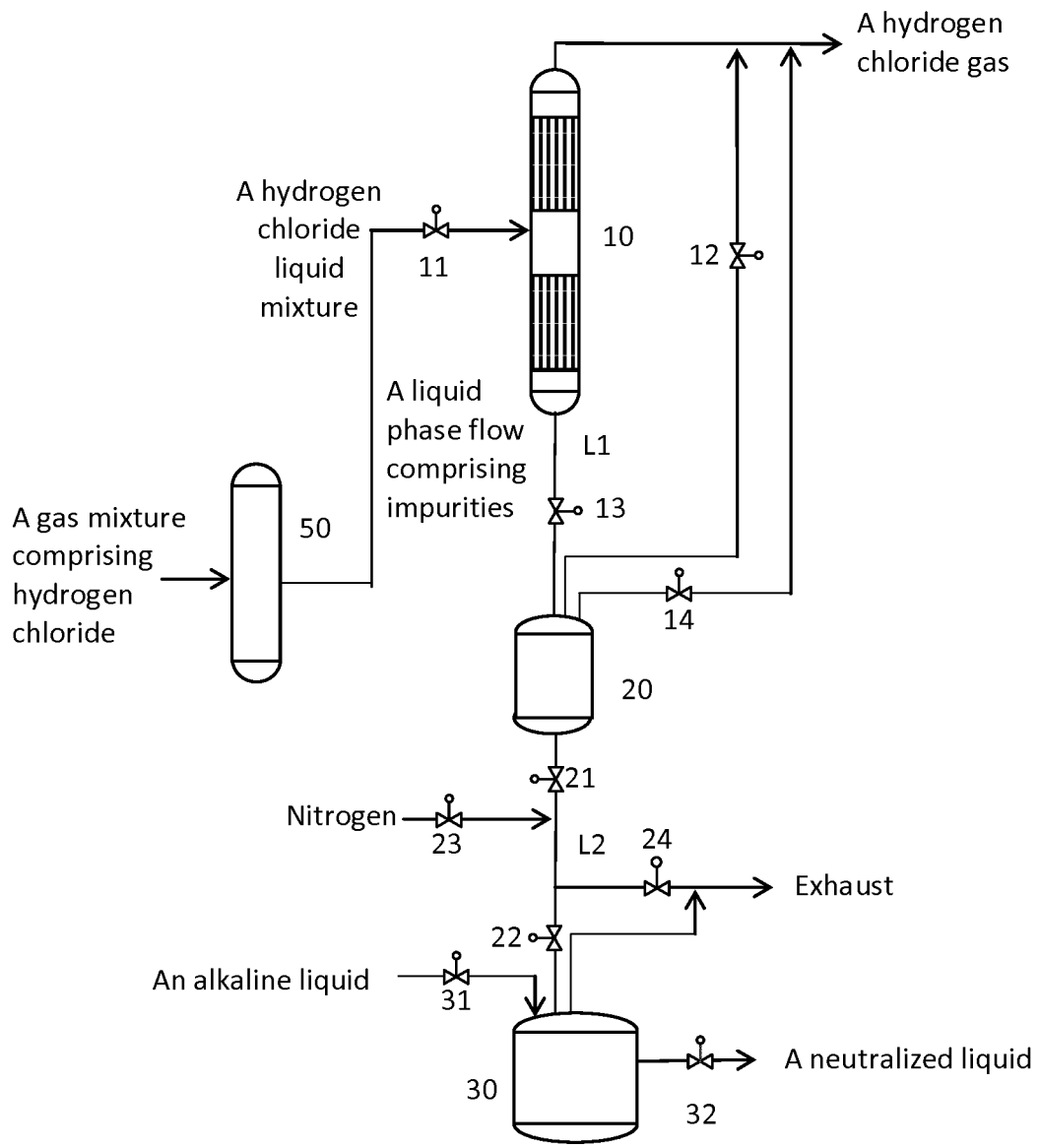
FIG. 5 is an exemplary figure of the system for preparing isocyanate with phosgenation in accordance with one Example of the present invention.

FIG. 5 is an exemplary figure of the system for preparing isocyanate with phosgenation in accordance with one Example of the present invention. The gas mixture comprising hydrogen chloride obtained by a phosgenation reaction process enters a hydrogen chloride rectification column 50. The hydrogen chloride rectification column 50 is connected with a gas-liquid separation column 10. The gas-liquid separation column 10 is longitudinally connected with a buffer tank 20 through a liquid phase flow pipeline L1. The gas-liquid separation column 10 is equipped with a pressure control valve 11 for controlling the pressure of the gas-liquid separation column 10. The liquid phase flow pipeline L1 is equipped with an discharge valve 13 which allows the liquid phase flow to flow into the buffer tank 20 from the gas-liquid separation column 10. The buffer tank 20 is equipped with a pressure balance valve 12 for keeping the pressures of the gas-liquid separation column 10 and the buffer tank 20 in balance. The buffer tank 20 is equipped with a pressure relief valve 14 for reducing the pressure of the buffer tank 20. The buffer tank 20 is longitudinally connected with a neutralization tank 30 through a liquid phase flow pipeline L2. The liquid phase flow pipeline L2 is equipped with an upper discharge valve 21 and a lower discharge valve 22, which allow the liquid phase flow to flow into the neutralization tank 30 from the buffer tank 20. The liquid phase flow pipeline L2 is further equipped with a nitrogen purge valve 23 and an exhaust discharge valve 24 which are used to purge and remove the liquid phase flow comprising impurities remained in the liquid phase flow pipeline L2 after the liquid phase flow comprising impurities flows through the liquid phase flow pipeline L2. The neutralization tank 30 is equipped with an alkaline liquid feed valve for adding alkaline liquid. The neutralization tank 30 is further equipped with a liquid discharge valve 32 for allowing the neutralized solution in the neutralization tank 30 to enter the waste liquid treatment device for treatment.

The gas-liquid separation column, buffer tank, neutralization tank and waste liquid treatment device described in the present invention, e.g. can be those common in the industries and are available in the market.

EXAMPLES

To further illustrate the present invention, the following Examples are provided.

Example 1

According to the process shown by FIG. 1, a hydrogen chloride liquid mixture at atmospheric pressure entered a gas-liquid separation column 10. The hydrogen chloride liquid mixture in the gas-liquid separation column 10 was heated to 50° C. to yield a liquid phase flow comprising impurities. The liquid phase flow comprising impurities flowed into a neutralization tank 30 which contained a sodium hydroxide solution having a concentration not less than 20 g/L through a vertical liquid phase flow pipeline L1. In the neutralization tank 30, the liquid phase flow comprising impurities had a neutralization reaction with the sodium hydroxide solution, yielding a neutralized solution. When the pH of the neutralized solution was stable at a value not less than 10, a liquid discharge valve 32 was opened to allow the neutralized solution to enter an incinerator for incineration. After the device working for half a year, no obvious deposition was observed in the gas-liquid separation column 10, the liquid phase flow pipeline and the valve.

Example 2

According to FIG. 4, a hydrogen chloride liquid mixture at a gauge pressure of 15 barg entered the gas-liquid separation column 10. The hydrogen chloride liquid mixture in the gas-liquid separation column 10 was heated to 80° C. to separate the hydrogen chloride liquid mixture to yield a gas phase flow comprising hydrogen chloride gas and a liquid phase flow comprising impurities. An upper discharge valve 21 and a lower discharge valve 22 were opened to allow the liquid phase flow comprising impurities to flow into the neutralization tank 30 through a vertical liquid phase flow pipeline L1. The upper discharge valve 21 was closed and the nitrogen purge valve 23 was opened to allow the nitrogen to flow through the liquid phase flow pipeline L1 to purge and remove the liquid phase flow comprising impurities remained in the liquid phase flow pipeline. Then the lower discharge valve 22 was closed and an exhaust discharge valve 24 was opened, after which the nitrogen purge valve 23 and the exhaust discharge valve 24 were closed. An alkaline liquid feed valve 31 was opened to introduce a sodium hydroxide solution having a concentration not less than 20 g/L into the neutralization tank 30. In the neutralization tank 30, the liquid phase flow comprising impurities had a neutralization reaction with the sodium hydroxide solution, yielding a neutralized solution. After the pH of the neutralized solution was stable at a value not less than 8, the liquid discharge valve 32 was opened to allow the neutralized solution to enter an incinerator for incineration. After the device working for half a year, no obvious deposition was observed in the gas-liquid separation column 10, the liquid phase flow pipeline and the valves.

Example 3

According to FIG. 5, a hydrogen chloride liquid mixture at a gauge pressure of 15 barg entered the gas-liquid separation column 10. The hydrogen chloride liquid mixture in the gas-liquid separation column 10 was heated to 80° C. to separate to yield a liquid phase flow comprising impurities. The liquid phase flow comprising impurities was accumulated at the bottom of the gas-liquid separation column 10. When the liquid level of the gas-liquid separation column 10 reached 30%, a pressure balance valve 12 was opened to balance the pressures of the gas-liquid separation column 10 and the a buffer tank 20. An discharge valve 13 was opened to allow the liquid phase flow comprising impurities to flow into the buffer tank 20 through a vertical liquid phase flow pipeline L1. The pressure balance valve 12 and the discharge valve 13 were closed. A pressure relief valve 14 was opened for slowly reducing the pressure of the buffer tank 20 to 3.5 barg, and then the pressure relief valve 14 was closed. An alkaline liquid feed valve 31 was opened to introduce a sodium hydroxide solution having a concentration not less than 20 g/L into the neutralization tank 30. The lower discharge valve 22 and the upper discharge valve 21 were opened to allow the liquid phase flow comprising impurities to flow into the neutralization tank 30 through a vertical liquid phase flow pipeline L2 and to have a neutralization reaction with the sodium hydroxide solution in the neutralization tank 30 to yield a neutralized solution. After the pH of the neutralized solution was stable at a value not less than 8, the liquid discharge valve 32 was opened to allow the neutralized solution to enter the incinerator for incineration. After the device working for half a year, no obvious deposition was observed in the gas-liquid separation column 10, the liquid phase flow pipeline and the valves.

Example 4

According to FIG. 5, an isocyanate product and a hydrogen chloride gas mixture comprising impurities were obtained by a phosgenation process. The gas mixture comprising hydrogen chloride entered the hydrogen chloride rectification column 50, yielding a hydrogen chloride liquid mixture. The pressure of the hydrogen chloride liquid mixture having a temperature of −10° C. and a pressure of 18 barg from the hydrogen chloride rectification column 50 was reduced to 15 barg by a pressure control valve 11. The hydrogen chloride liquid mixture entered the gas-liquid separation column 10. The hydrogen chloride liquid mixture in the gas-liquid separation column 10 was heated to 80° C. to separate the hydrogen chloride liquid mixture to a gas phase flow comprising hydrogen chloride gas and a liquid phase flow comprising impurities. The liquid phase flow comprising impurities was accumulated at the bottom of the gas-liquid separation column 10. When the liquid level of the gas-liquid separation column 10 reached 60%, the pressure balance valve 12 was opened to balance the pressures of the gas-liquid separation column 10 and the a buffer tank 20. The discharge valve 13 was opened to allow the liquid phase flow comprising impurities to flow into the buffer tank 20 through a vertical liquid phase flow pipeline L1 from the gas-liquid separation column 10. The pressure balance valve 12 and the discharge valve 13 were closed. A pressure relief valve 14 was opened for slowly reducing the pressure of the buffer tank 20 to 3.5 barg, and then the pressure relief valve 14 was closed. An alkaline liquid feed valve 31 was opened to introduce a sodium hydroxide solution having a concentration not less than 20 g/L into the neutralization tank 30. Then the lower discharge valve 22 and the upper discharge valve 21 were opened to allow the liquid phase flow comprising impurities to flow into the neutralization tank 30 through a vertical liquid phase flow pipeline L2 from the buffer tank 20. The upper discharge valve 21 was closed and a nitrogen purge valve 23 was opened to allow the nitrogen gas to pass the liquid phase flow pipeline L2 and the liquid phase flow comprising impurities remained in the liquid phase flow pipeline L2 was purged and removed. Then the lower discharge valve 22 was closed and the exhaust discharge valve 24 was opened, after which the nitrogen purge valve 23 and the exhaust discharge valve 24 were closed. In the neutralization tank 30, the liquid phase flow comprising impurities had a neutralization reaction with the sodium hydroxide solution, yielding a neutralized solution. After the pH of the neutralized solution was stable at a value not less than 8, the liquid discharge valve 32 was opened to allow the neutralized solution to enter an incinerator for incineration. The gas phase flow comprising hydrogen chloride gas was purified by a hydrogen chloride absorption column and then recycled to the phosgenation reactor for using. After the device working for half a year, no obvious deposition was observed in the gas-liquid separation column 10, the liquid phase flow pipeline and the valves.

According to the system for separating and treating impurities from a hydrogen chloride liquid mixture of the above examples of the invention, the liquid phase flow pipeline, valve and gas-liquid separation column contain less impurity deposition and the shutdown frequency for maintenance is reduced.

Although the present invention has disclosed the relatively good Examples as above, they are not used to limit the present invention. Any person skilled in this technology can make alternations and modifications, provided that they do not deviate from the spirit and the scope of the present invention. Therefore, the protection scope of the present invention shall be based on the claims sought for patent protection.

The invention claimed is:
1. A method of separating and treating impurities from a hydrogen chloride liquid mixture, comprising the steps of:
sending said hydrogen chloride liquid mixture comprising impurities into a gas-liquid separation column for separation to yield a liquid phase flow comprising impurities at the bottom of said gas-liquid separation column, and said impurities comprising ammonium chloride;
making said liquid phase flow comprising impurities flow into a neutralization tank, neutralizing said liquid phase flow comprising impurities with an alkaline liquid in said neutralization tank to yield a neutralized solution; and
sending the neutralized solution into a waste liquid treatment device from said neutralization tank for treatment, and obtaining said hydrogen chloride liquid mixture from a process for preparing isocyanate with phosgenation.
2. The method according to claim 1, wherein said neutralization tank is arranged below said gas-liquid separation column, and the pressure in said neutralization tank is not higher than the pressure in said gas-liquid separation column.
3. The method according to claim 1, wherein a buffer tank is further arranged between said gas-liquid separation column and said neutralization tank, such that said liquid phase flow comprising impurities sequentially flows into said buffer tank from the bottom of said gas-liquid separation column through a first liquid phase flow pipeline L1, and then flows into the neutralization tank through a second liquid phase flow pipeline L2 from said buffer tank.
4. The method according to claim 3, wherein said buffer tank is arranged below said gas-liquid separation column, and said neutralization tank is arranged below said buffer tank, the pressure in said buffer tank being not higher than the pressure in said gas-liquid separation column, and the pressure in said neutralization tank is not higher than the pressure in said buffer tank.

5. The method according to claim 3, wherein the volume of said liquid phase flow comprising impurities buffered in said buffer tank does not exceed 90% of the volume of said buffer tank.

6. The method according to claim 1, wherein the liquid phase flow comprising impurities flows into the neutralization tank through a liquid phase flow pipeline L1 from the bottom of said gas-liquid separation column, and wherein the liquid phase flow pipeline is purged with an inert gas after said liquid phase flow comprising impurities flows through said liquid phase flow pipeline.

7. The method according to claim 1, wherein the pH value of said neutralized solution is not less than 8.

8. The method according to claim 1, wherein said alkaline liquid comprises a base selected from one or more of the following group consisting of: alkali metal hydroxides, and alkaline earth metal hydroxides.

9. The method according to claim 1, wherein said method is a continuous or batch operation.

10. A system for separating and treating impurities from a hydrogen chloride liquid mixture, comprising:
    a gas-liquid separation column having a top and a bottom, an inlet stream comprising a liquid mixture of hydrogen chloride and impurities comprising ammonium chloride, an outlet stream comprising hydrogen chloride gas at the top of the gas-liquid separation column, a first liquid phase flow outlet stream at the bottom of the gas-liquid separation column, wherein the first liquid phase flow comprises impurities comprising ammonium chloride, and a first liquid phase flow pipeline connected to the bottom of the gas-liquid separation column;
    a neutralizing tank connected via the first liquid phase flow pipeline to the bottom of the gas-liquid separation column for receiving said first liquid phase flow comprising impurities,
    and neutralizing said liquid phase flow comprising impurities with an alkaline liquid in said neutralization tank to yield a neutralized solution; and
    a waste liquid treatment device for receiving and treating said neutralized solution from said neutralization tank
    wherein the system further comprises a pipeline for a hydrogen chloride liquid mixture from a production site for preparing isocyanate with phosgenation which comprises the inlet stream comprising the liquid mixture of hydrogen chloride and impurities comprising ammonium chloride.

11. The system according to claim 10, wherein the pressure in said neutralization tank is not higher than the pressure in said gas-liquid separation column.

12. The system according to claim 10, further comprising an inert gas purge valve for purging said first liquid phase flow pipeline with an inert gas after said first liquid phase flow comprising impurities flows through the first liquid phase flow pipeline.

13. A method of preparing isocyanate with phosgenation, comprising the steps of:
    obtaining an isocyanate product and a gas mixture comprising hydrogen chloride from a phosgenation reaction process;
    treating said gas mixture comprising hydrogen chloride to yield a hydrogen chloride liquid mixture; and
    separating and treating said hydrogen chloride liquid mixture according to the method of claim 1.

14. A system for preparing isocyanate with phosgenation, comprising:
    a phosgenation reaction unit for carrying out a phosgenation reaction to yield an isocyanate product and a gas mixture comprising hydrogen chloride;
    a hydrogen chloride-containing gas mixture treatment unit for treating said gas mixture comprising hydrogen chloride to yield a hydrogen chloride liquid mixture; and
    a hydrogen chloride liquid mixture separation and treatment unit for separating and treating said hydrogen chloride liquid mixture according to the system of claim 10.

15. A system for separating and treating impurities from a hydrogen chloride liquid mixture, comprising:
    a gas-liquid separation column having a top and a bottom, an inlet stream comprising a liquid mixture of hydrogen chloride and impurities comprising ammonium chloride, an outlet stream comprising hydrogen chloride gas at the top of the gas-liquid separation column, a first liquid phase flow outlet stream at the bottom of the gas-liquid separation column, wherein the first liquid phase flow comprises impurities comprising ammonium chloride, and a first liquid phase flow pipeline connected to the bottom of the gas-liquid separation column;
    a buffer tank connected via the first liquid phase flow pipeline, for buffering said first liquid phase flow comprising impurities,
    a neutralizing tank connected to the buffer tank via a second liquid phase flow pipeline, for neutralizing the buffered liquid phase flow comprising impurities with an alkaline liquid to form a neutralized solution;
    wherein the first liquid phase flow comprising impurities sequentially flows into said buffer tank from the bottom of said gas-liquid separation column through said first liquid phase flow pipeline, and then flows into the neutralization tank through the second liquid phase flow pipeline from the buffer tank,
    a waste liquid treatment device for receiving and treating the neutralized solution from the neutralization tank and
    wherein the system further comprises a pipeline for a hydrogen chloride liquid mixture from a production site for preparing isocyanate with phosgenation which comprises the inlet stream comprising the liquid mixture of hydrogen chloride and impurities comprising ammonium chloride.

16. The system according to claim 15, wherein the pressure in the gas-liquid separation column is from 5 to 25 bar gauge pressure, and the pressure in the buffer tank is from 0 to 10 bar gauge pressure.

* * * * *